US006771736B2

(12) United States Patent
Sabol et al.

(10) Patent No.: US 6,771,736 B2
(45) Date of Patent: Aug. 3, 2004

(54) METHOD FOR DISPLAYING TEMPORAL CHANGES IN SPATIALLY MATCHED IMAGES

(75) Inventors: John M. Sabol, Sussex, WI (US); Gopal B. Avinash, New Berlin, WI (US); Vianney Pierre Battle, Milwaukee, WI (US); Kadri Nizar Jabri, Waukesha, WI (US); Renuka Uppaluri, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 179 days.

(21) Appl. No.: 10/064,548

(22) Filed: Jul. 25, 2002

(65) Prior Publication Data

US 2004/0017892 A1 Jan. 29, 2004

(51) Int. Cl.[7] .............................................. G01N 23/083
(52) U.S. Cl. ........................ 378/98.12; 378/8; 378/901
(58) Field of Search ............................ 378/4, 8, 15, 62, 378/98.2, 98.12, 901

(56) References Cited

U.S. PATENT DOCUMENTS 6,064,770 A * 5/2000 Scarth et al. ............... 382/225

* cited by examiner

Primary Examiner—David V Bruce
(74) Attorney, Agent, or Firm—Artz & Artz, PC

(57) ABSTRACT

A temporal image processing system includes a temporal processing controller receiving at least two images temporally spaced apart, from a scanning unit. The temporal processing controller includes a registration module, which registers a region of interest within the images and generates therefrom a registration signal. The temporal processing controller further includes a confidence module receiving the registration signal and generating a confidence map therefrom. The confidence map enhances contrast of temporal changes in the object relative to a contrast due to misregistrations.

20 Claims, 4 Drawing Sheets

METHOD FOR DISPLAYING TEMPORAL CHANGES IN SPATIALLY MATCHED IMAGES

BACKGROUND OF INVENTION

The present invention relates generally to imaging systems and more particularly to a method to improve the display of temporal changes, imaging devices, such as x-ray machines, are widely used in both medical and industrial applications. Imaging devices often use temporal processing to track change in an object over time.

Temporal processing systems typically include the following general modules: acquisition storage module, segmentation module, registration module, comparison module, and reporting module. The input images are 1-D, 2-D, 3-D, derived, synthesized, or montaged, where multiple separate images from a single time point are combined to provide a larger composite, seamless image. Additionally, 1-D images can be montaged to produce 2-D and 3-D images, for example a CT scout-view.

The detection of change in medical images of a patient acquired at two different instances in time has great potential for improving diagnosis. The advent of digital imaging allows computer-assisted detection and identification of these changes and the creation of a "dissimilarity image" containing the change information. This dissimilarity image can be read by a human reader or can become the input to an automated analysis device such as a CAD (computer assisted diagnosis) algorithm.

Currently, as part of Mitsubishi Space Software's "temporal subtraction" application, dissimilarity images are calculated using a simple pixel-by-pixel subtraction of registered images. Simple subtraction, however, results in images with poor contrast, and is not substantially robust when the two initial images are acquired using different techniques. Simple subtraction also does not incorporate an indication of the confidence in the magnitude of the dissimilarity measurement.

For a temporal subtraction image, the resulting pixel values (and hence the displayed gray-levels) are proportional to the difference or dissimilarity in pixel value between two input images acquired with temporal separation.

Input images are often registered and processed to compensate for several factors such as: the difference in positioning of the subject during the two image the difference in acquisition parameters, the difference in the bit resolution of the images, and the differences in any pre or post processing that may have been applied to the images.

Any errors in registration of the two images may result in significantly large values in the dissimilarity image. For example, if the resulting registration is not perfect, the temporal analysis image of a subject that is identical at both imaging times, is not uniform whereas the desired result is an image with no contrast. Non-zero elements appear at the positions where the registration was not exact. These non-zero elements represent artifacts that could be mistaken for a temporal change in the subject.

Even an ideal registration algorithm produces artifacts, if for no other reason than noise in the image acquisition process. With a poorly chosen display mapping, differences in the noise texture between the two temporally separated images are visible and potentially distracting to the observer. In the case of imperfect registration, it is possible that errors in registration will be displayed with higher contrast than physical changes in the patient.

The disadvantages associated with current, imaging systems have made it apparent that a new technique for temporal processing and display is needed. The new technique should substantially increase accuracy of information acquired obtained from temporal processing. The present invention is directed to this end.

SUMMARY OF INVENTION

In accordance with one aspect of the present invention, a temporal image processing system includes a temporal processing controller adapted to receive a first image signal and a second image signal from an image controller. The temporal processing controller includes a registration module adapted to register a region of interest of the first image signal and the second image signal and generate therefrom a registration signal. The temporal processing controller further includes a confidence module adapted to receive the registration signal and further adapted to determine a confidence map therefrom. The confidence map is adapted to enhance a contrast of a temporal change in the object relative to a contrast due to at least one misregistration.

In accordance with another aspect of the present invention, a temporal image processing method includes scanning an object and generating a first image signal and a second image signal therefrom. The method further includes receiving the first image signal and the second image signal in a registration module and registering at least one region of interest of the first image signal and the second image signal such that at least one cost signal is generated. A confidence map is generated from the cost signal thereby enhancing a temporal change contrast between the first image signal and the second image signal. At least one distinction is generated between a contrast of temporal changes between the first image signal and the second image signal and a contrast resultant from at least one misregistration.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

The present invention is illustrated with respect to a temporal image processing system 10, particularly suited to the medical field, specifically to chest x-ray imaging. The present invention is, however, applicable to various other uses that may require temporal imaging, such as non-destructive testing and other industrial applications, as will be understood by one skilled in the art.

Figure 1:
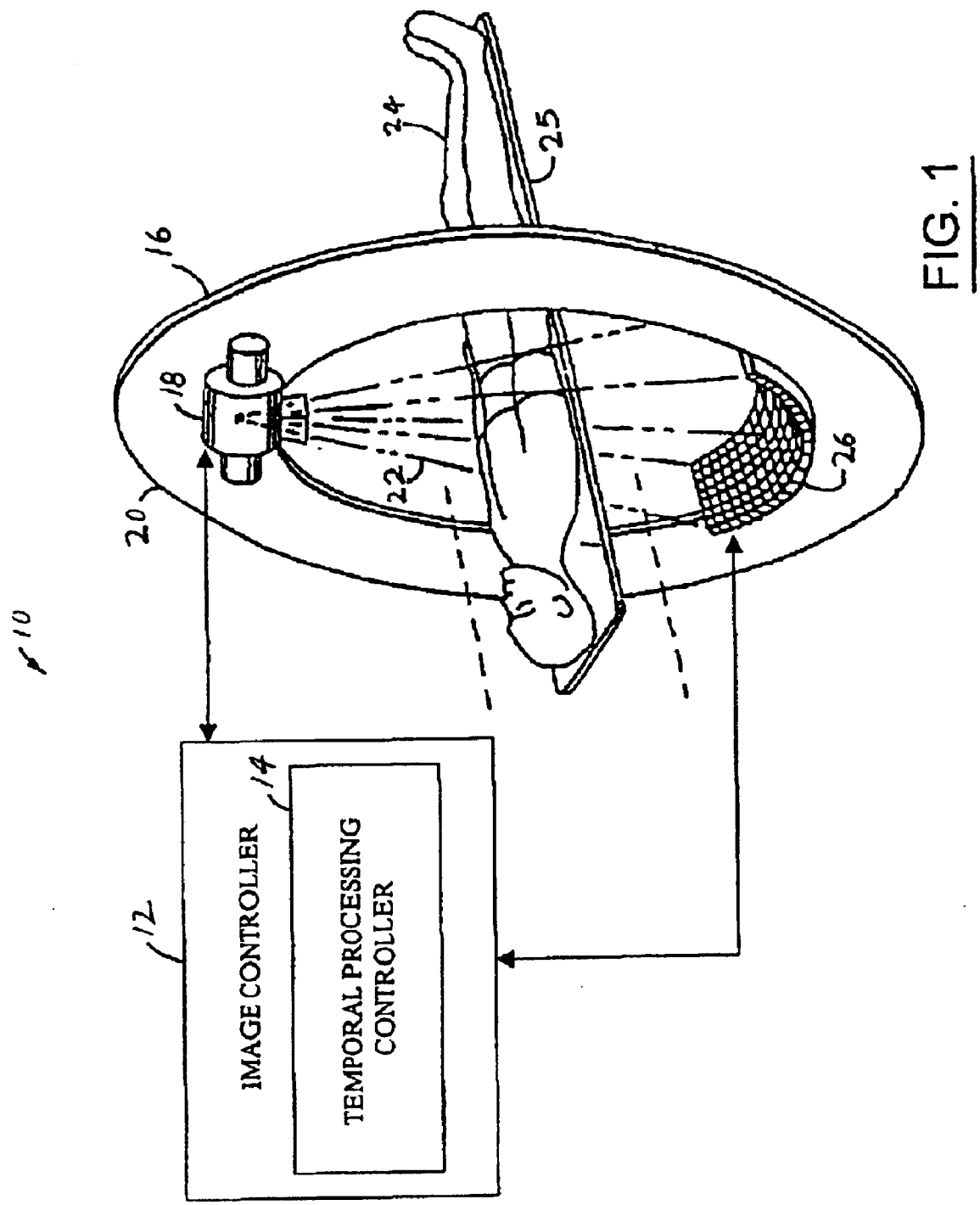
FIG. 1 is a diagram of an imaging system in accordance with a preferred embodiment of the present invention.
Figure 2:
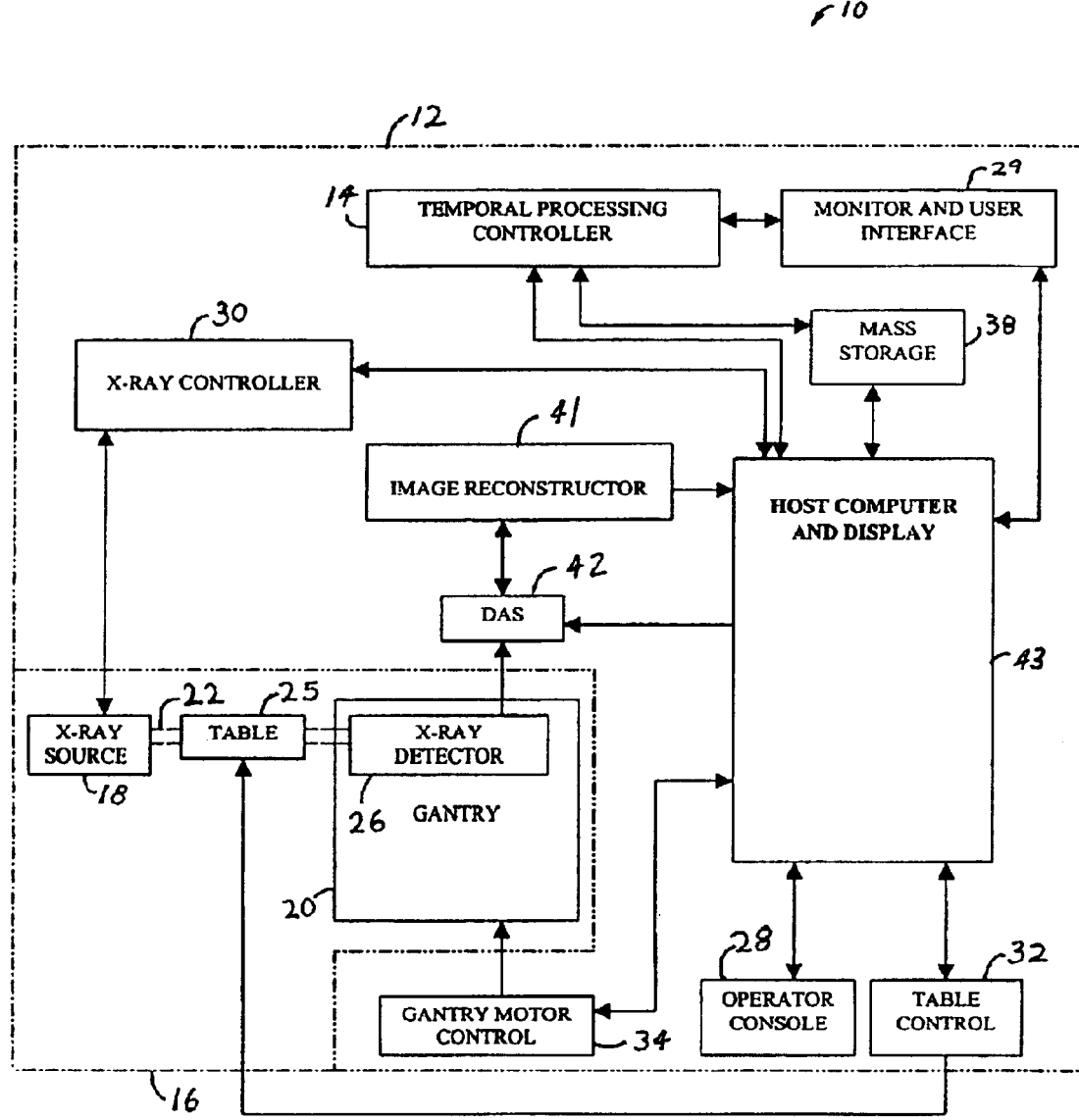
FIG. 2 is a schematic diagram of FIG. 1.

Referring to FIGS. 1 and 2, an image controller 12, including a temporal processing controller 14, coupled to a scanning unit 16, in accordance with a preferred embodiment of the present invention, is illustrated. The scanning unit 16 includes, for example, an x-ray source 18 coupled to a gantry 20, generating an x-ray flux 22, which passes through an object 24 (e.g. a patient) on a table 25. The system 10 further includes an x-ray detector 26, also coupled to the gantry 20.

The image controller 12, including the temporal processing controller 14 and various other widely known imaging control and display components, receives the detector signals and responds by generating a first and a second image signal. The imaging controller 12 also includes, for example, an operator console 28, a monitor and user interface 29 an x-ray controller 30, a table control 32, a gantry motor control 34, a mass storage 38, an image reconstructor 41 and a data acquisition system (DAS) 42, all of which couple to a host computer and display 43, are well known in the art, and will be discussed later.

Figure 3:
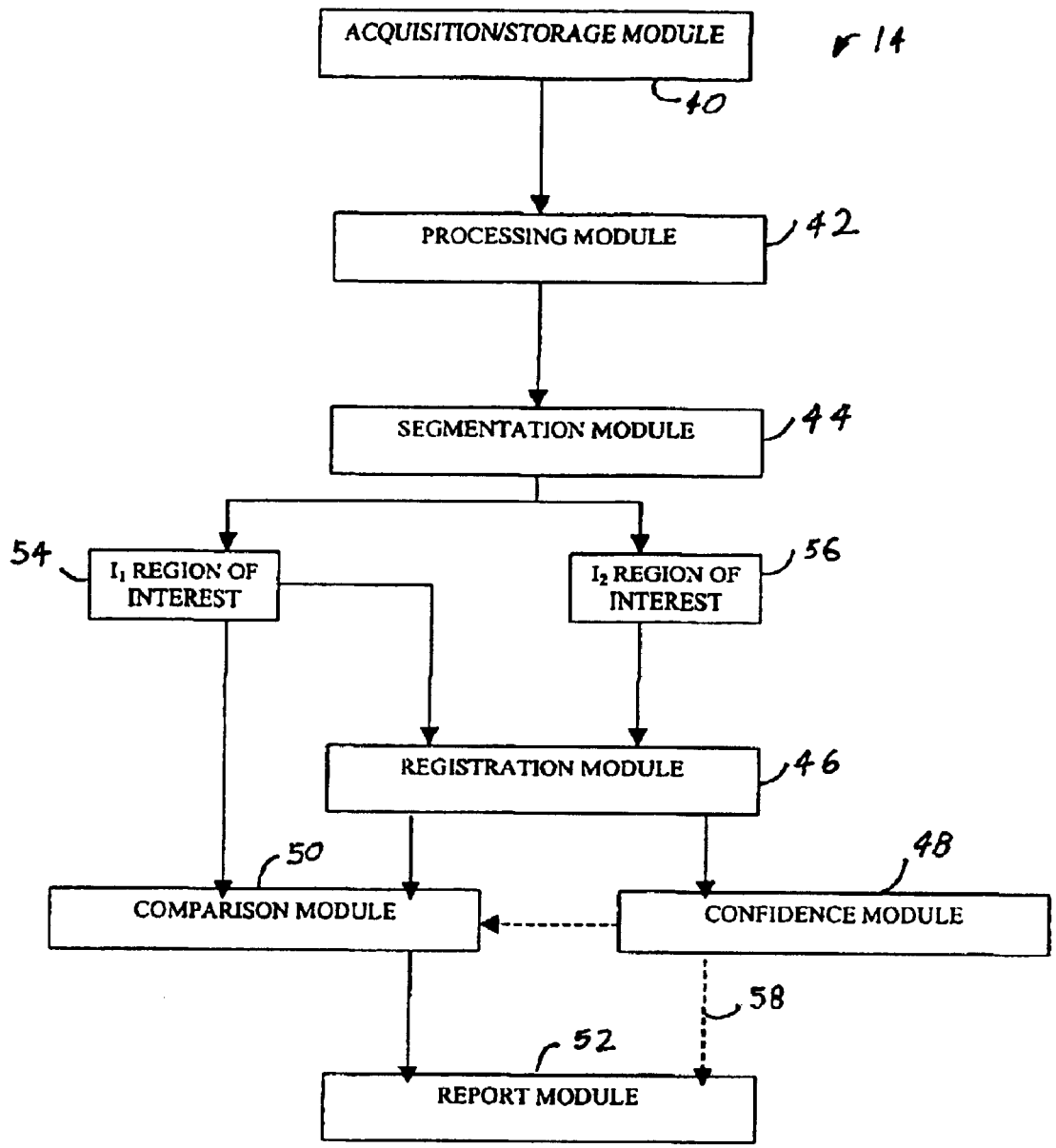
FIG. 3 is a schematic diagram of the temporal processing unit of FIG. 1.

Referring to FIG. 3, a schematic diagram of the temporal processing controller 14 of FIG. 1 is illustrated. One embodiment of the temporal imaging controller 14 includes an acquisition storage module 40, a processing module 42, a segmentation module 44, a registration module 46, a confidence module 48, a comparison module 50, and a report module 52. The aforementioned modules are either software algorithms or discrete circuit components or a combination thereof, as will be understood by one skilled in the art.

Referring to FIGS. 1, 2 and 3, the acquisition storage module 40 contains the acquired images. For temporal change analysis, a data retrieval system retrieves the data from storage (e.g. the mass storage unit 38) corresponding to an earlier time point or from the image reconstructor 41, which receives signals from the data acquisition system (DAS) 42.

As an illustrative example, only two images $I_1$ and $I_2$ corresponding to two time points $t_1$ and $t_2$ are included, however one skilled in the art will realize that the general approach can be extended for any number of images in the acquisition and temporal sequence. The temporal comparison image is denoted as $I_{1-2}$. $I_1$ and $I_2$, are either the original unprocessed images from an acquisition system or alternately, post-processed versions of the original images. One skilled in the art will realize that the acquisition storage module 40 can include images from almost any digital imaging, source including digitized versions of analog, film images.

The processing module 42 receives the two images, $I_1$ and $I_2$, from the acquisition storage module 40 and "normalizes" them to account for differences in acquisition techniques or differences in pre- and post-processing methods. To illustrate, in x-ray images, if the first image $I_1$ has half the exposure of the second image $I_2$, the gray levels in the first image are multiplied by two before any further comparison to the second image. This multiplication adjusts for the differences in overall image intensity due to, for example, differences in x-ray dose.

The segmentation module 44 receives the normalized images from the processing module 42 and, through automated or manual operation in the user interface 29 or operator console 28, isolates regions of interest of $I_1$ 54 and $I_2$ 56. Often is the case that the entire image is the region of interest.

The registration module 46 receives the region of interest signals 54, 56 from the segmentation module 44 and provides methods of registration and therefrom generates a registration signal. If the regions of interest 54, 56 for temporal change analysis are small, rigid body registration transformations including translation, rotation, magnification, and shearing are sufficient to register a pair of images from $t_1$ and $t_2$. If, however, the regions of interest 54, 56 are large including almost the entire image, warped, elastic transformations are applied.

One way to implement the warped registration is to use a multi-scale, multi-region, pyramidal approach. For this approach, a different cost function highlighting changes is optimized at every scale. Such cost functions are correlation methods, such as mathematical correlation and sign-change measurement, or statistical methods such as entropy measurements and mutual information.

For warped registration, images are re-sampled at a given scale and subsequently divided into multiple regions. Separate shift vectors are calculated for different regions. Shift vectors are interpolated to produce a smooth shift transformation, which is applied to warp one of the images. The images $I_1$, $I_2$ are re-sampled and the warped registration process repeats at the next higher scale until the predetermined final scale is reached. In other situations, a combination of rigid registration and elastic transformations is used.

The confidence module 48 receives the cost function and a figure of merit of the cost function and uses them to determine a confidence map. The resulting map enhances the contrast of temporal changes in the object relative to the contrast due to misregistrations. This highlights anatomical changes relative to minor errors in registration. It is important to note that the cost function provides extreme values irrespective of whether the non-zero pixel values in the dissimilarity image are due to inadequacy of the registration methods or due to true anatomical changes.

An alternate embodiment includes separating out whether the change was due to anatomical change or due to inaccuracies in registration. This is accomplished in several different methods. All these methods make use of the prior knowledge of the object 24, the anticipated modes of motion, or the anticipated disease-state.

For example, the bones in the object 24 tend to move as rigid bodies, objects within an organ or tissue structure tend to move together in a smooth and continuous manner. Knowledge of the characteristic shape, expected extent, etc of a disease state is alternately used. For example, for detecting nodules, circularity metric in 2D or sphericity metric in 3-D is used with anticipated limits on these metrics.

The comparison module 50 receives the $I_1$ region of interest signal 54 and the registration signal, computes a dissimilarity measure between the registered images, and therefrom generates a comparison signal.

Registered image comparison is performed in several ways. In addition to, or instead of, using a simple subtraction between the registered images to get the dissimilarity image, an enhanced division method is used, which is described as $(I\_1*I\_2)/(I\_2*I\_2+\phi)$.

The confidence image applies to at least two embodiments. In the first embodiment, the confidence map is integral to the creation of a dissimilarity image. For example, in one embodiment of the present invention, Phi ($\phi$) is spatially dependant upon the confidence map. To provide additional flexibility, a sensitivity metric determines the relative strength of the confidence weighting. This is illustrated by the dotted line connecting the confidence module and the comparison module. The user control or other known control device adjusts the relative importance thereof. The control is embedded within the application or adapted for user operation.

For example, by extreme adjustment of the control, a user calculates a pure dissimilarity image (all changes are equally weighted), or by the opposite extreme adjustment of the control the user calculates a scaled dissimilarity image in which the pixel values are scaled relative to the confidence that they represent anatomical changes and not registration errors.

In the second embodiment, the confidence map is used only to weigh the display such that the image resulting from the enhanced division combines with the previously derived confidence information, as discussed below in regards to the report module 52.

The report module 52 receives the comparison signal and provides the display and quantification capabilities for the user to visualize and quantify the results of temporal comparison. Results of temporal comparisons are simultaneously displayed on a second display unit with either image $I_1$ or $I_2$. Or a superposition of $I_{1-2}$ onto $I_1$ or $I_2$ generates with a logical operator based on pre-specified criterion, as will be understood by one skilled in the art. For quantitative comparison, color look-up tables for the overlaid images are used as an illustrative example. Alternate quantitative comparison techniques include numerical classification, segmentation of the different image sections, or other known discrete identification techniques. The resulting combination is realized with a multi-color overlay display.

Another way to combine change and confidence information is to modify locally the dissimilarity image, based on the confidence map. Such modifications affect, locally, the colors used to display the difference image or the gray level contrast itself.

To provide additional flexibility, a sensitivity metric determines the relative strength of the confidence weighting. This is illustrated by the dotted line connecting the confidence module and the report module 58. The user control adjusts the sensitivity metric relative importance.

For example, through extreme adjustment, the Monitor 29 displays a pure dissimilarity image (all changes are equally weighted), or through the opposite extreme adjustment of user control, the monitor 29 displays a scaled dissimilarity image in which the pixel values are scaled relative to the confidence that they represent anatomical changes and not registration errors. This display incorporates either color, numerical or other known methods for distinguishing characteristics to highlight regions of interest.

In addition to observer display, the resultant images are further analyzed quantitatively. For example the use of other statistical measures, such as entropy, or pattern recognition techniques including CAD perform further automated analysis of the results.

The present invention is illustrated with respect to x-ray and computed tomography (CT) systems, however it is alternately used for any type of imaging system including magnetic resonance imaging (MRI), mammography, vascular x-ray imaging, bone scanning, PET, radionuclide imaging, ultrasound imaging, optical imaging, etc. Further embodiments include non-medical applications, such as weld inspection and metal inspection. Essentially, anything application that uses an system to make 1, 2 or 3 dimensional images or 1, 2, or 3 dimensional montaged images is included.

Typical scanning units include an x-ray source 18 coupled to a gantry 20. The x-ray source 18 generates an x-ray flux 22, which passes through a scanned object 26 on a table 25. An x-ray detector 26 is also typically coupled to the gantry 20 such that the detector 26 receives the x-ray flux 22. Detector specific corrections or calibrations are then engaged, as will be understood by one skilled in the art.

The x-ray source 18 is embodied as a flat panel x-ray source or an extended x-ray source (e.g. imatron), or a standard x-ray tube. The x-ray source 18 is activated by either the host computer 43 or an x-ray controller 30, as will be understood by one skilled in the art. The x-ray source 18 sends the x-ray flux 22 through the object 24 on the moveable table 25 controlled by the table control device 32 acting in response to signals from the host computer 43, as will be understood by one skilled in the art.

The embodied gantry 20 is a ring shaped platform that rotates around the scanned object 24 in response to signals from the gantry motor control 34, as will be understood by one skilled in the art.

For a single image $I_1$, the x-ray flux 22 from the x-ray source 18 passes through the object 24 and impinges on the x-ray detector 26. The signal passes to the host computer and display 43, where the signal is converted to a gray level corresponding to the attenuation of an x-ray photon through the patient. The image is then stored in the mass storage unit 38 or received in the temporal imaging controller 14.

The detector 26 is typically located opposite the x-ray source 18 to receive x-ray flux 22 generated therefrom.

The host computer 43 receives detector signals. The host computer 43 also activates the x-ray source 18 through signals from the operator console 28 or user interface 29; however, alternate embodiments include independent activation means for the x-ray source 18. The present invention includes an operator console 28 for control by technicians, as will be understood by one skilled in the art.

One embodiment of the present invention incorporates use of temporal imaging for the scout scan on an imaging system 10. During a scout scan from the x-ray source 18 to the detector elements 26, the x-ray tube remains stationary while the patient table 25 translates under the x-ray flux 22. This results in a two-dimensional image ideal for qualitative information and for locating the desired position for scanning during further temporal imaging.

Figure 4:
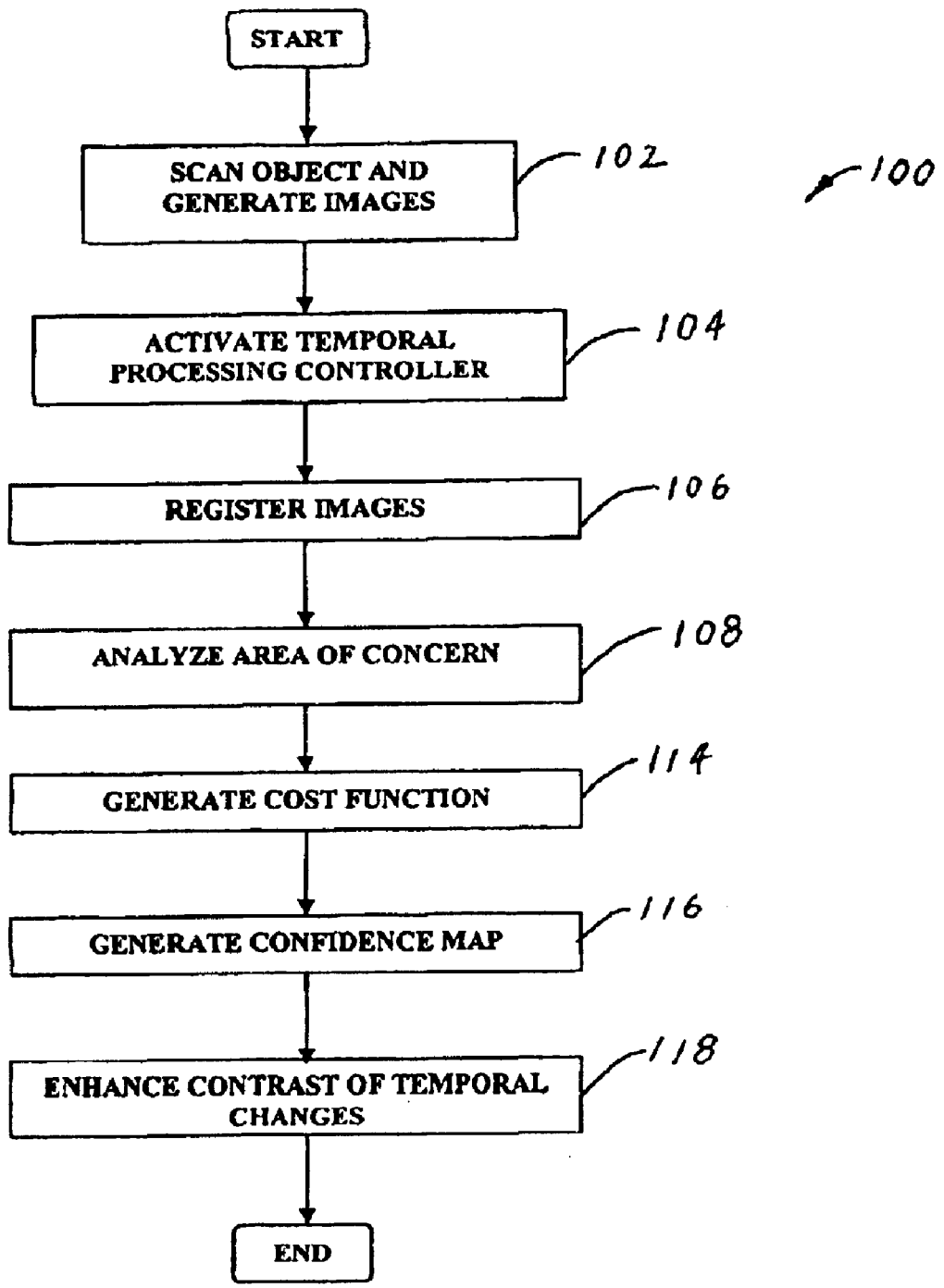
FIG. 4 is a block diagram of a temporal image processing method, in accordance with a preferred embodiment of the present invention.

Referring to FIG. 4, a block diagram of a temporal image processing method 100 is illustrated. Logic starts in operation block 102 where the object is scanned at different periods of time to generate image signals.

Operation block 104 then activates, and the temporal processing controller acquires the image signals through the acquisition storage module, normalizes the images in the processing module, and isolates regions of interest in the segmentation module. Operation block 106 then activates, and the temporal processing controller registers the images.

In operation block 108 the region or area of concern is analyzed. Minor regions are analyzed with at least one of translation criteria, rotation criteria, magnification criteria, or shearing criteria, thereby generating a cost signal (i.e. cost function or a figure of merit of the cost function) in operation block 114.

Major areas are analyzed through at least one warped transformation criterion, thereby generating a cost signal (i.e. cost function or a figure of merit of the cost function).

In operation block 114, the cost signal from a major region or a minor region is used to generate a confidence map in operation block 116.

Operation block 118 activates, and at least one distinguishing characteristic between the contrast of temporal changes between the images and contrast due to misregistration is generated.

A critical piece of temporal subtraction technology is the display of the results to the observer. It is critical that the observer understands the display processing chain. As such, even though the mapping of subtraction results to displayed gray levels is likely to consist of embedded software, not accessible to the end-user, the specifics of the algorithm is disclosed so that the observer understands at what is viewed and can judge the clinical significance of the displayed gray levels using prior knowledge of the process and understanding of imaging physics, anatomy, and pathology.

The additional inclusion of a user variable, or exam dependant sensitivity metric to determine the relative strength of the confidence weighting provides additional flexibility. Since the user chooses to view anything from a pure dissimilarity image to dissimilarity image scaled relative to confidence in registration the user becomes familiar with the system and learn to judge the clinical significance of the displayed changes.

In operation, the temporal image processing method includes scanning an object and generating a first image signal and a second image signal therefrom. A registration module receives the signals, and registers at least one region of interest of the first image signal and the second image signal such that at least one cost signal is generated. A confidence map is generated from the cost signal thereby enhancing a temporal change contrast between the first image signal and the second image signal. At least one distinguishing characteristic between a contrast of temporal changes between the first image signal and the second image signal and a contrast resultant from at least one misregistration is also generated.

From the foregoing, it can be seen that there has been brought to the art a new temporal image processing system 10. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

What is claimed is:

1. A temporal image processing system comprising:
   a temporal processing controller adapted to receive a first image signal and a second image signal from a scanning unit,
   said temporal processing controller comprising a registration module adapted to register a region of interest of said first image signal and said second image signal, said registration module further adapted to generate therefrom a registration signal, said temporal processing controller further comprising a confidence module adapted to receive said registration signal and further adapted to determine a confidence map therefrom, said confidence map adapted to enhance a contrast of a temporal change in said object relative to a contrast due to at least one misregistration.

2. The system of claim 1, wherein for said region of interest comprising a minor region of said object, at least one rigid body registration transformation including at least one of translation, rotation, magnification, or shearing is a criterion used to register said first image signal and said second image signal.

3. The system of claim 1, wherein for said region of interest including a major region of said object, at least one warped transformation is a criterion used to register said first image signal and said second image signal.

4. The system of claim 3, wherein said at least one warped transformation is implemented through multi-region, multi-scale, pyramidal logic designed such that a different cost function is adapted to highlight changes between said first image signal and said second image signal for a plurality at each of a plurality of scales.

5. The system of claim 4, wherein said cost function includes at least one of mathematical correlation, sign-change measurement, or statistical analysis.

6. The system of claim 1, wherein said confidence module is adapted to receive at least one of said cost function and a figure of merit of said cost function, said confidence module further adapted to generate said confidence map therefrom.

7. The system of claim 1, wherein said confidence module is adapted to distinguish whether a difference between said first image signal and said second image signal is resultant from an anatomical change or said at least one misregistration.

8. The system of claim 1, further comprising a sensitivity metric adapted to regulate a relative importance of said confidence map.

9. A temporal image processing method comprising:
   scanning an object and generating a first image signal and a second image signal therefrom;
   receiving said first image signal and said second image signal in a registration module;
   registering at least one region of interest of said first image signal and said second image signal such that at least one cost signal is generated;
   generating a confidence map from said cost signal thereby enhancing a temporal change contrast between said first image signal and said second image signal; and
   generating at least one distinguishing characteristic between a contrast of temporal changes between said first image signal and said second image signal and a contrast resultant from at least one misregistration.

10. The method of claim 9 wherein generating further comprises generating a first image signal including a one-dimensional image, two-dimensional image, three-dimensional image, one-dimensional montage image, two-dimensional montage image, or three-dimensional montage image.

11. The method of claim 9 wherein generating a confidence map further comprises generating a confidence map from a cost function or figure of merit of said cost function.

12. The method of claim 9 wherein registering further comprises registering a minor region of interest of said object within said first image signal and said second image signal with at least one of translation criteria, rotation criteria, magnification criteria, or shearing criteria.

13. The method of claim 9 wherein registering further comprises registering a major region of interest of said object within said first image signal and said second image signal through at least one warped transformation criterion.

14. The method of claim 13 wherein registering further comprises registering a major region of interest of said object within said first image signal and said second image signal through at least one warped transformation criterion including multi-region, multi-scale, pyramidal logic; and
   highlighting changes between said first image signal and said second image signal with a different cost function at each of a plurality of scales.

15. The method of claim 14, wherein said cost function includes at least one of mathematical correlation, sign-change measurement, or statistical analysis.

16. The method of claim 9 wherein generating a confidence map from said cost signal further comprising receiving in said confidence module at least one of a cost function or a figure of merit of said cost function; and generating a confidence map from said at least one of said cost function or a figure of merit of said cost function.

17. The system of claim 9, further comprising illustrating a difference between said first image signal and said second image signal according to whether said difference is resultant from an anatomical change or said at least one misregistration.

18. The system of claim 9, further comprising regulating a relative importance of said confidence map with a sensitivity metric, which is either embedded or adapted for user operation.

19. A temporal image processing system comprising:

a scanning unit adapted to scan an object and generate a first image signal and a second image signal of said object; and an image controller coupled to said scanning unit and adapted to receive said first image signal and said second image signal, said image controller comprising a temporal processing controller adapted to receive said first image signal and said second image signal in a registration module, register at least one region of interest of said first image signal and said second image signal such that at least one cost signal is generated, generate a confidence map from said cost signal thereby enhancing a temporal change contrast between said first image signal and said second image signal, and generate at least one distinguishing characteristic between a contrast of temporal changes between said first image signal and said second image signal and a contrast resultant from at least one misregistration.

20. The system of claim 19, wherein said scanning unit comprises one of a CT scanning unit, an x-ray scanning unit, an MRI scanning unit, a PET, a radionuclide imaging system, an ultrasound imaging unit, or an optical imaging unit.

* * * * *